United States Patent
Chandler et al.

[11] Patent Number: 5,935,156
[45] Date of Patent: Aug. 10, 1999

[54] METHOD AND APPARATUS FOR ADMINISTERING MICROCURRENT ELECTROTHERAPY TREATMENT

[75] Inventors: Mark H. Chandler, Pinehurst, N.C.; Carl M. Marino, Carlisle, Pa.

[73] Assignee: Microleve International, Ltd., Addlestone, United Kingdom

[21] Appl. No.: 08/815,684

[22] Filed: Mar. 12, 1997

[51] Int. Cl.[6] .................................................. A61N 1/18
[52] U.S. Cl. .............................................................. 607/66
[58] Field of Search .................................. 607/66, 68, 71, 607/50, 75, 72, 46, 70

[56] References Cited

U.S. PATENT DOCUMENTS

| | | | |
|---|---|---|---|
| 2,004,751 | 6/1935 | Fischer et al. | 607/71 |
| 4,919,139 | 4/1990 | Brodard | 607/70 |
| 5,047,007 | 9/1991 | McNichols et al. | 607/70 |

*Primary Examiner*—William E. Kamm
*Assistant Examiner*—George R. Evanisko
*Attorney, Agent, or Firm*—Rhodes, Coats, & Bennett, LLP

[57] ABSTRACT

The present invention relates to a microcurrent electrotherapy device that is pre-programmed to produce a series of different microcurrent waveform signals that are directed to a selected treatment area of a human or animal. More particularly, the electrotherapy device is pre-programmed to produce a sequence of different pulsed and continuous direct microcurrent waveforms. In one programmed mode, the programmed electrotherapy device produces a pulsed direct current waveform of approximately 10 $\mu$A to 100 $\mu$A which is followed by a second treatment phase of a direct microcurrent of approximately 300 $\mu$A to 1000 $\mu$A which is followed by a third treatment phase of pulsed direct microcurrent of approximately 50 to 250 $\mu$A.

23 Claims, 5 Drawing Sheets

METHOD AND APPARATUS FOR ADMINISTERING MICROCURRENT ELECTROTHERAPY TREATMENT

FIELD OF THE INVENTION

The present invention relates generally to a method and apparatus for aiding in pain relief and promoting healing in injured tissues using electrical current. More particularly, this invention relates to a microcurrent electrotherapy treatment program involving the sequential application of at least three different electric profiles and an apparatus therefor.

BACKGROUND OF THE INVENTION

The application of electrical energy to injured tissues has been an acceptable mode of medical therapy for many years and is well characterized. For instance, U.S. Pat. No. 4,846,181 to Miller, issued on Jul. 11, 1989, lists eleven technical articles on the subject of electrotherapy. Those articles suggest, among other ideas, that: application of electrical stimulation can promote wound healing; that electrical stimulation can be applied to wounds in the presence of saline; that low intensity direct current can be utilized as the applied electrical stimulation; that applied low intensity direct current stimulation can be switched between negative and positive polarities during the course of treatment; that high voltage, low amperage galvanic stimulation can be applied for short treatment pulses that are periodically repeated.

In addition, several patents have also been issued directed to promoting healing by electrical stimulation. Included in these patents are the following:

| Patent Number | Inventor | Issue Date |
| --- | --- | --- |
| 2,099,511 | Caesar | 11/16/37 |
| 3,918,459 | Horn | 11/11/75 |
| 3,964,477 | Ellis et al | 6/22/76 |
| 4,019,510 | Ellis | 4/26/77 |
| 4,233,965 | Fairbanks | 11/18/80 |
| 4,312,340 | Donadelli | 01/26/82 |
| 4,313,438 | Greatbatch | 02/02/82 |
| 4,314,554 | Greatbatch | 02/09/82 |
| 4,556,051 | Maurer | 12/3/85 |

The above-listed patents include showings that: electrical stimulation can utilize preselected treatment times between a few minutes to a few hours; the polarity of the active electrode can be switched during the course of treatment, and that pulses can be utilized as electrical stimulation.

U.S. Pat. No. 4,989,605 to Rossen discloses an example of known transcutaneous electrical nerve stimulation (TENS) devices. The Rossen device outputs between 25 microamps to 9000 microamps of a monophasic sequence of bursts of a D.C. carrier signal (10,000 Hz to 19,000 Hz) which is modulated off and on in time at a frequency selected from the range 0.3 Hz to 10,000 Hz. The Rossen device's bursts are characterized as having a periodicity greater in duration than that associated with the modulation frequency. In addition, Rossen suggests reversing the polarity of the electrodes periodically during treatment.

Another patent, U.S. Pat. No. 5,397,338 to Grey et. al., discloses another electrotherapy device for pain control and the promotion of tissue healing. The Grey device is capable of operating in either TENS mode, Microcurrent Electrical Neuromuscular Stimulation (MENS) mode, or in Iontophoresis mode. The modes are distinguished from each other based on the electrical waveform produced. For instance, the iontophoresis mode utilizes D.C. burst waveforms with currents of from 100 microamps to 4 milliamps. The TENS mode utilizes a positive biphasic or alternating monophasic waveform with currents of from 20 microamps to 20 milliamps. The MENS mode utilizes a monophasic waveform with currents of from 10 microamps to 150 microamps. The Grey device is intended as a multi-purpose unit capable of operating in various modes without requiring the changing of electronic stimulation units or electrodes between modes. However, changing from one mode to another in the Grey device is accomplished by manually altering switch positions, thus the Grey unit does not automatically change from one mode to another.

Existing electrotherapy methods utilize the above described devices, or variations thereof, to subject the tissue to be treated to a particular electrotherapy treatment. Typically, these treatments utilize only a single waveform and/or current setting for the duration of the treatment.

SUMMARY OF THE INVENTION

The present invention improves upon the prior electrotherapy methods by subjecting the tissue to be treated to series of waveform/current treatment stages so as to better promote healing or pain relief. The method of the present invention includes engaging an area of the body to be treated with a plurality of electrodes, then treating that area of the body by directing in sequence a series of different microcurrent treatments to the area being treated. In one embodiment of the present invention, a pulsed direct current of between 10 $\mu$A and 100 $\mu$A having a frequency of between 100 and 500 Hz is directed to the treatment area during a first treatment stage. In a second treatment stage, a continuous direct current of between 300 $\mu$A and 1000 $\mu$A is applied to the area to be treated. In a third treatment stage, a pulsed direct current of between 50 $\mu$A and 250 $\mu$A having a frequency of between 1 and 10 Hz and a duty cycle of between 30 and 70 percent is directed to the treatment area.

With respect to the method of administering microcurrent electrotherapy to a body area, the method of the present invention comprises the step of sequentially directing to a body area being treated a series of different and programmed microcurrent treatments wherein the programmed microcurrent treatments sequentially administered include both a pulsed direct and continuous direct microcurrent treatments.

It is therefore an object of the present invention to provide a microcurrent electrotherapy device that is programmed to produce in sequence a series of different microcurrent waveforms for treating a selected body area of a patient.

Other objects and advantages of the present invention will become apparent and obvious from a study of the following description and the accompanying drawings which are merely illustrative of such invention.

DETAILED DESCRIPTION OF THE INVENTION

Figure 1:
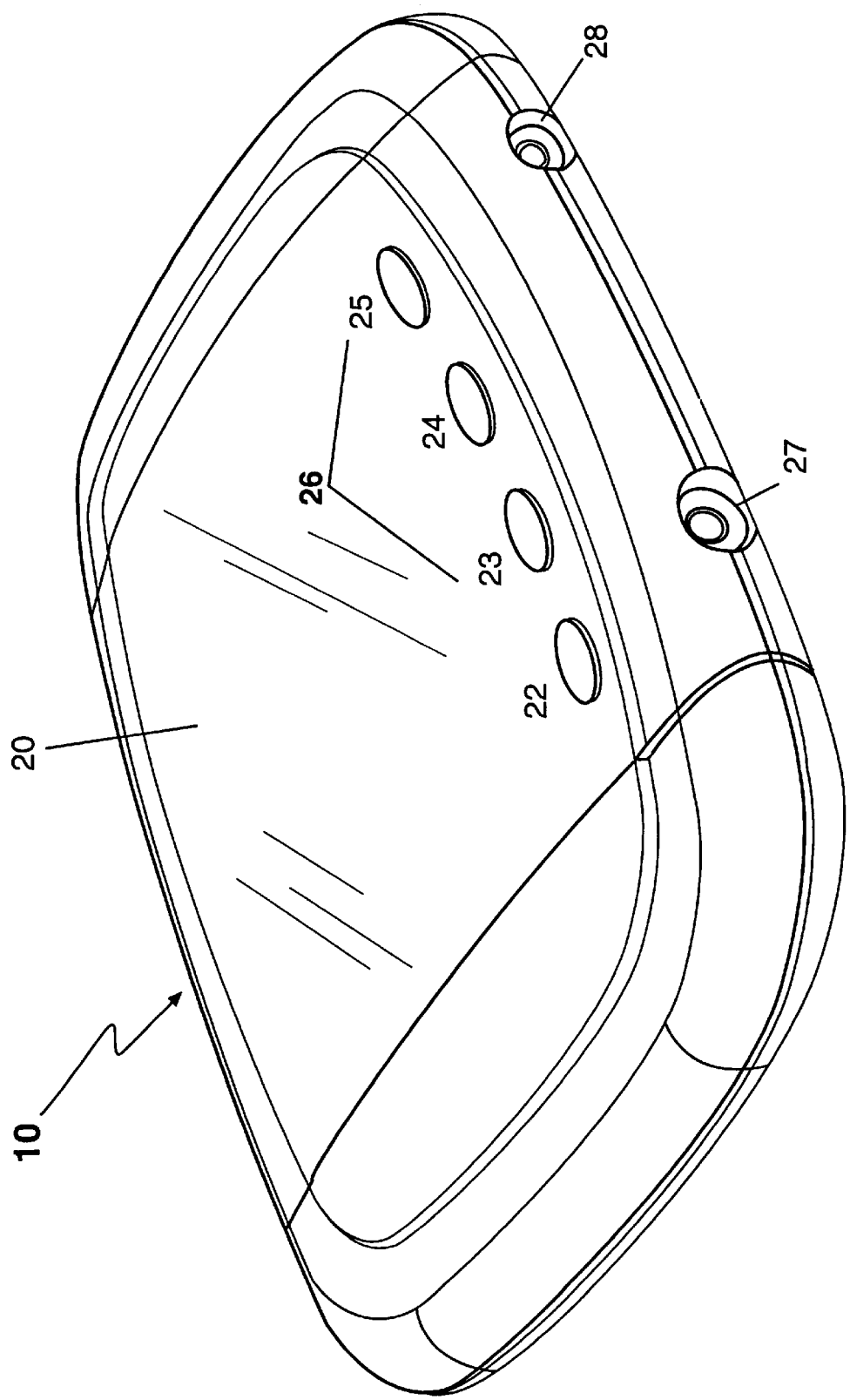
FIG. 1 is a perspective view of the electrotherapy device of the present invention.

FIG. 1 shows the electrotherapy device 10 of the present invention. Preferably, the electrotherapy device 10 includes a primary channel 30 and a secondary channel 130 encased in an outer shell 20 equipped with a primary electrode port 27, and a secondary electrode port 28.

Figure 2:
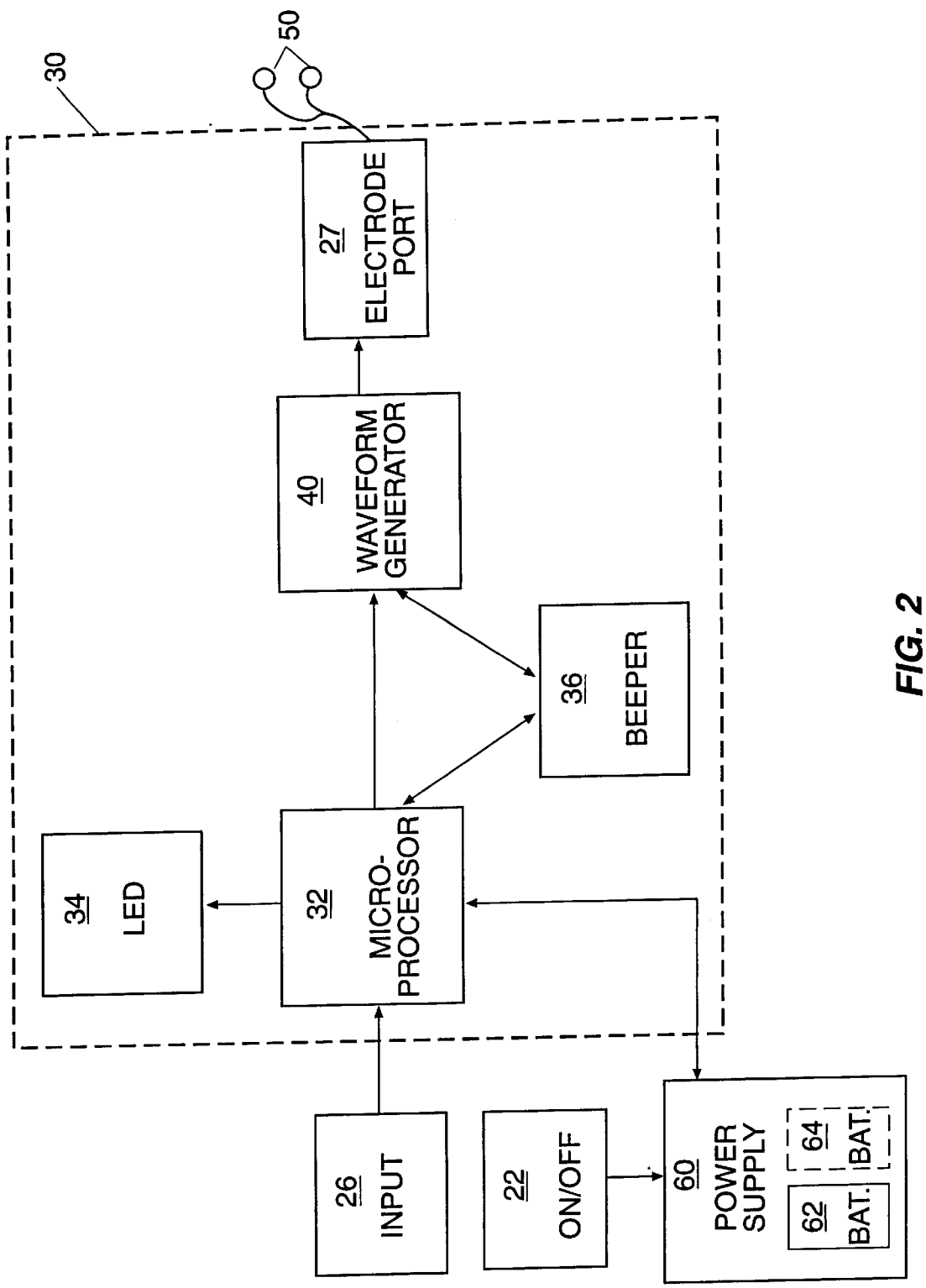
FIG. 2 is a block diagram illustrating the functional components of a typical electrical circuit of the present invention with one output channel.

FIG. 2 shows the basic electronic operating configuration of the primary channel 30 of the present invention. The primary channel 30 includes a primary electrode port 27, a microprocessor 32, LEDs 34, a beeper 36, and a waveform generator 40. Connected to the primary channel 30 are an on/off switch 22, input switches 23, 24, 25 (collectively 26), the primary electrodes 50, and a power supply 60. The input switches 26 and the on/off switch 22 are preferably push button type and resistor multiplexed into an analog to digital port of the microprocessor 32. The primary electrodes 50 can be of any type known in the art of microcurrent electrotherapy; the particular details of the electrodes 50 are not necessary to understanding the present invention.

The power supply 60 supplies the microprocessor 32 and rest of the primary channel 30 with power. The power supply 60 includes a primary battery 62 and, optionally, a secondary battery 64. The primary battery 62 supplies power to the primary channel 30. If present, the secondary battery 64 provides power to a secondary channel 130. Turning on the device 10 via the on/off switch 22 activates the power supply 60, which in turn controls the on/off state of the battery 62. In a preferred embodiment the power supply 60 converts the battery voltage to a supply logic level of five volts.

The microprocessor 32 controls and/or monitors voltage, input switches 23, 24, 25, status LEDs 34, beeper 36, and the waveform generator 40. The waveform generator 40 takes signals from the microprocessor 32, transforms them into the appropriate microcurrent waveforms, and supplies the waveforms to the primary electrode port 27. From the primary electrode port 27, the primary electrodes 50 carry the waveforms to the tissue to be treated.

Figure 3:
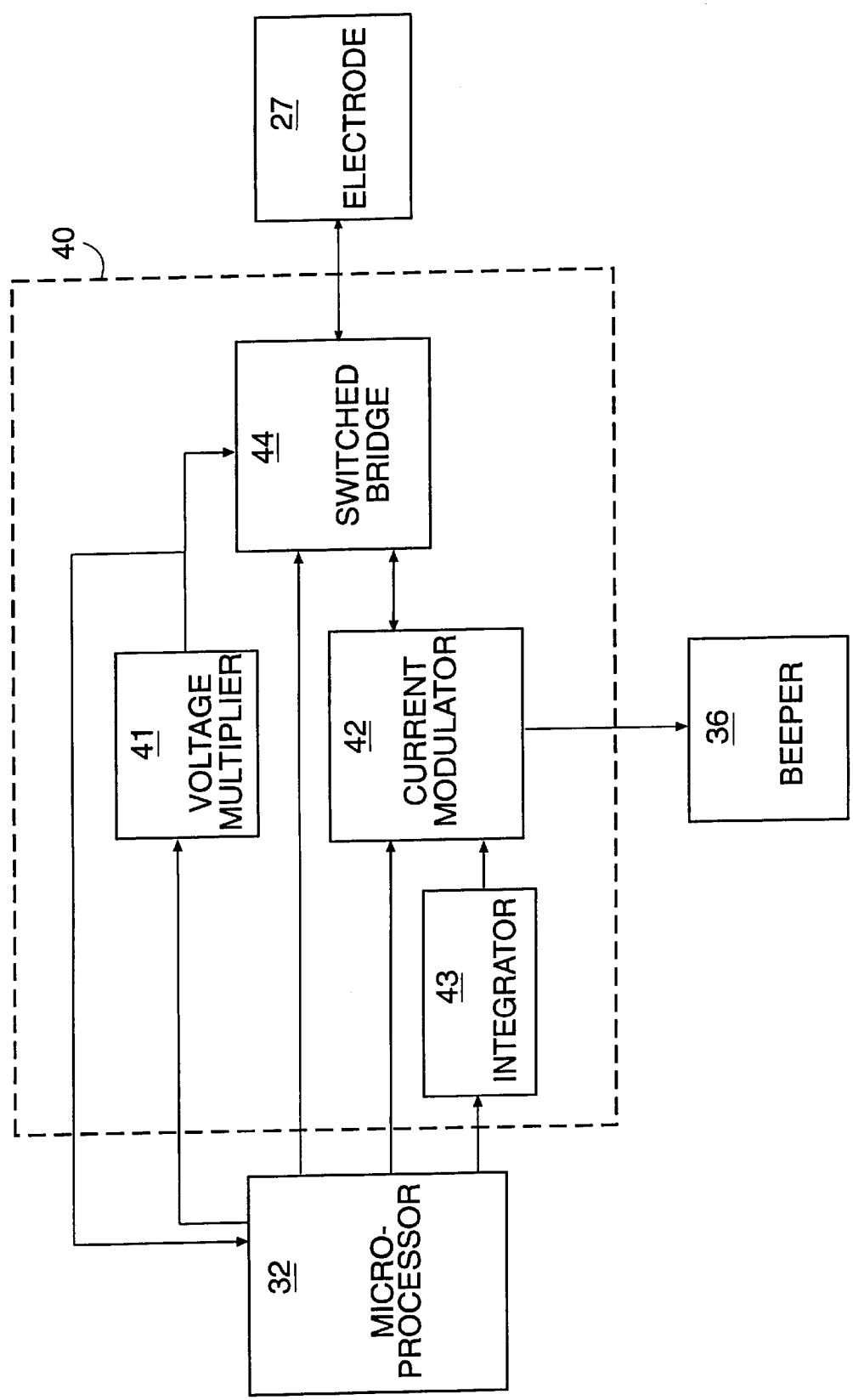
FIG. 3 is a block diagram illustrating the functional components of a waveform generator.

As shown in FIG. 3, the waveform generator 40 preferably includes a voltage multiplier 41, a current modulator 42, an integrator 43, and a switched bridge 44. The combined portions of the waveform generator 40 take power from the power supply 60 and generate a microcurrent electrotherapy waveform under direction from the microprocessor 32.

The voltage multiplier 41 supplies a voltage pumped signal to the switched bridge 44. Preferably, the voltage multiplier 41 includes a voltage feedback loop with the microprocessor 32. The switched bridge 44 supplies the generated microcurrent waveform to the primary electrode port 27. Preferably, the switched bridge 44 comprises four opto-isolators in a bridge configuration. In addition to the voltage pumped signal from the voltage multiplier 41, the switched bridge 44 receives an output polarity control signal from the microprocessor 32 and a current modulation signal from the current modulator 42. The integrator 43 manipulates the waveform signals received from the microprocessor 32 resulting in ramp, sine and square wave outputs as required. These outputs are sent on to the current modulator 42. The current modulator 42 controls the output current level under direction of the microprocessor 32. The current modulator 42 receives the signals from the integrator 43 and also receives numerous current control signals from the microprocessor 32.

The microprocessor 32 supplies different signals to various portions of the waveform generator 40 so as to generate the appropriate microcurrent electrotherapy waveforms. For instance, the microprocessor 32 supplies a modulated square wave signal to the voltage multiplier 41, an output polarity setting to the switched bridge 44, a pulse width modulated synthesized waveform to the integrator 43, and a current level selection signal to the current modulator 42.

The primary channel output from the device 10 is to the electrodes 50. These electrodes 50 are supplied electrical signals from the waveform generator 40 via the primary electrode port 27. The status of the device 10 is indicated by LEDs 34 which are controlled by the microprocessor 32. Also, the device 10 includes a warning beeper 36 which is controlled by the microprocessor 32. The warning beeper 36 is activated when the device 10 detects high resistance between the electrodes 50 of an electrode pair, indicating that the electrodes 50 are not making proper contact to the portion of the body to be treated. Such a situation is called a pad open condition.

From an inactivated state, the above identified device 10 is activated via the on/off switch 22. Once energized, the microprocessor 32 checks the other switches 23, 24, 25 to determine which one of various pre-programmed treatments has been selected. Based on the program selected, the microprocessor 32 sends the appropriate signals to the waveform generator 40 to cause the appropriate signals to be sent to the electrodes 50. The microprocessor also instructs the LEDs 34 and the beeper 36 to indicate the appropriate status. Once the selected treatment is completed, the unit automatically returns to a ready state. In addition, if the treatment selection is changed while another treatment is running, the microprocessor 32 will terminate the existing treatment and initiate the new treatment program.

In a preferred embodiment, the device 10 is pre-programmed to provide three different treatments depending on which of the input switches 23, 24, or 25 is selected. Switch 23 causes only a first treatment stage to be provided to the tissue to be treated. Switches 24 and 25 cause each of a first, second, and third treatment stages to be provided to the tissue to be treated and then terminates. Switch 24 provides a lower electrotherapy current level and switch 25 provides a higher electrotherapy current level. Preferably, the switch 24 current levels are 20 $\mu$A for the first treatment stage, 400 $\mu$A for the second treatment stage, and 60 $\mu$A the third treatment stage and switch 25 current levels are 20 $\mu$A for the first treatment stage, 650 $\mu$A for the second treatment stage, and 120 $\mu$A the third treatment stage. The waveforms and treatment stages are more fully discussed below.

Figure 4:
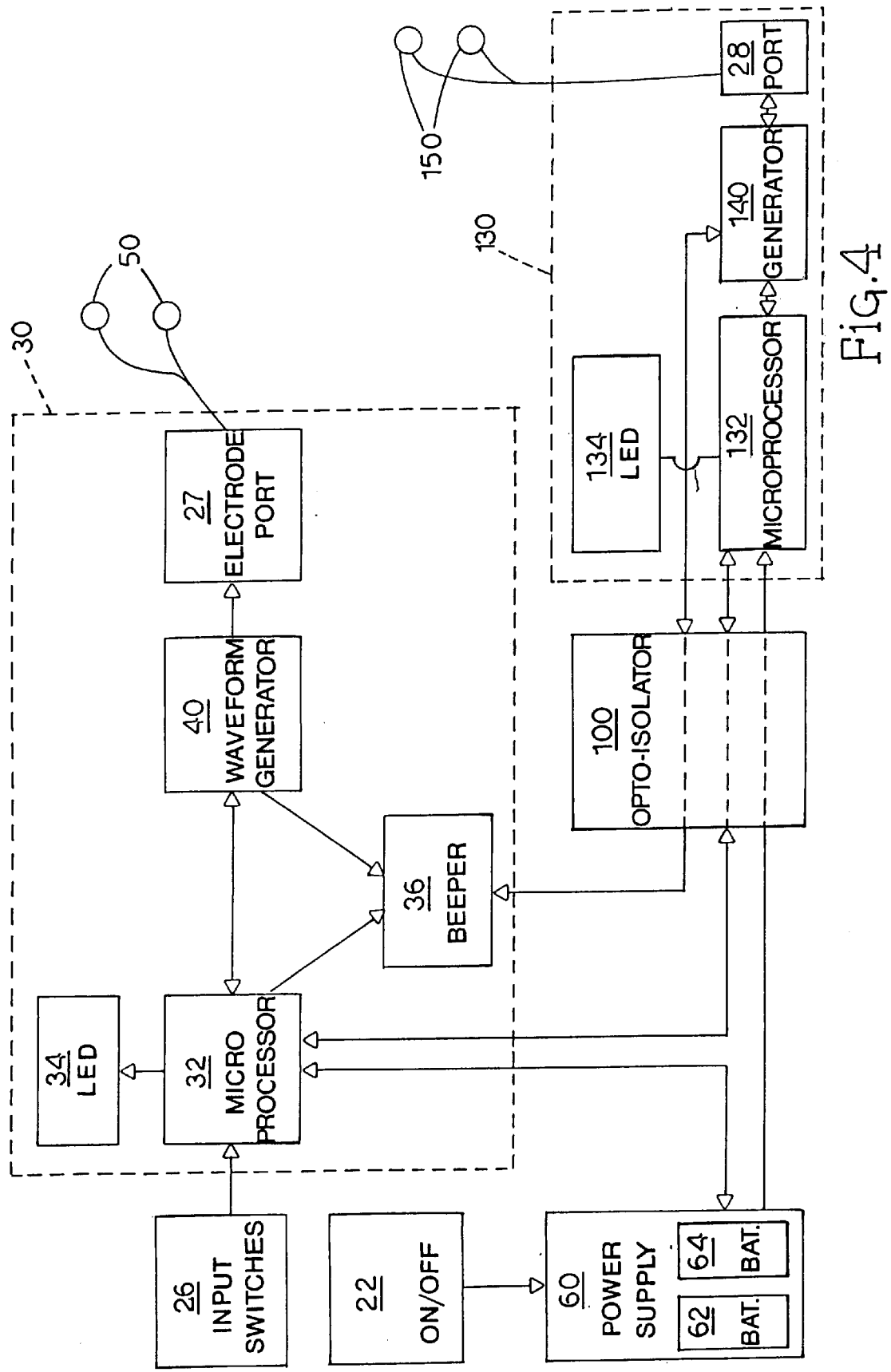
FIG. 4 is a block diagram illustrating the functional components of a typical electrical circuit of the present invention with two output channels.

The description above has focused on the primary channel 30. However, in a preferred embodiment, the device 10 also includes a secondary channel 130 within the same outer shell 20 as the primary channel 30 for simultaneously treating a second tissue area. A block diagram of a device having both a primary channel 30 and a secondary channel 130 is shown in FIG. 4. The secondary channel 130 includes a secondary microprocessor 132, a secondary waveform generator 140, secondary LEDs 134, and a secondary electrode port 28. The secondary channel 130 communicates with the primary channel 30 described above via an opto-isolator 100. The secondary channel 130 is configured and functions like the primary channel 30 except: 1) there are no additional input switches, the input switches 23, 24, 25 for the primary channel 30 communicate with both channels and 2) there is no additional beeper 36; pad open status for the secondary channel 130 is communicated to the primary channel beeper 36 via the opto-isolator 100. In addition, the secondary LEDs 134 indicate only battery status of the secondary battery 64. The secondary channel 130 has its own battery 64; power for the secondary circuit is derived from this battery 64. When the battery 64 is present, the secondary channel is activated whenever the primary channel 30 is active and supplies the same waveform to its own electrodes 150 via the secondary electrode port 28 as the primary channel 30 provides to its electrodes 50 via the primary electrode port 27. If the secondary battery 64 is not present (or is dead), the secondary channel 130 is not activated.

The method of the present invention relates to an electrotherapy method utilizing at least three different treatment stages applied sequentially so as to relieve pain and/or promote healing. During the three treatment stages, electrical signals are sent to an area of the body via electrodes 50, 150 which have been placed on either side of injured or painful tissue. The process is designed to function with one electrode pair 50, or with a plurality of electrode pairs such as a primary pair 50 and a secondary pair 150. For instance, a large area such as a knee might be treated with a plurality of electrode pairs, but a small area such as a single finger joint might be treated with a single electrode pair. In each case, the electrode pair(s) would be disposed such that the tissue to be treated would be interposed between the individual electrodes of each pair.

The present inventive method includes steps of arranging electrodes around the area of the body to be treated, supplying a first electrotherapy waveform in a first treatment stage, supplying a second electrotherapy waveform in a second treatment stage, and supplying a third electrotherapy waveform in a third treatment stage. After the third treatment stage, the process is complete. However, the process could obviously be restarted upon completion.

The first treatment stage is intended to help cleanse the injured tissue of toxins. In humans, the first treatment stage is particularly designed to stimulate the lymphatic system to facilitate cleansing. During this cleansing stage, the electrodes receive pulsed direct current impulses of between 10 $\mu$A and 100 $\mu$A having a frequency of between 100 and 500 Hz. Preferably, the impulses are of 20 $\mu$A at a frequency of 300 Hz. While the cleansing stage may last for longer or shorter periods, the preferred method is for this stage to last 5 to 10 minutes.

Figure 5:
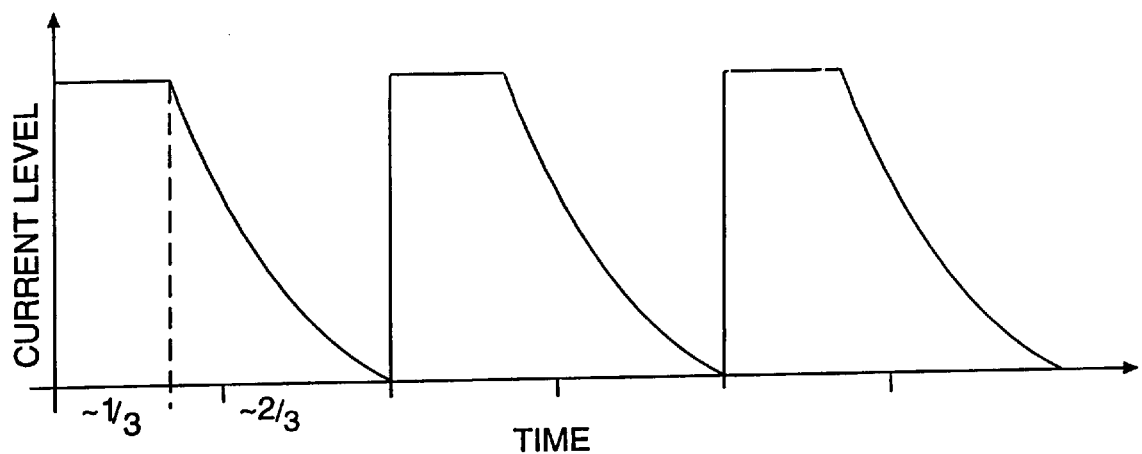
FIG. 5 is a simplified illustration of the features of the waveform of the electrical signal employed for each treatment stage according to the present invention.
Figure 5:
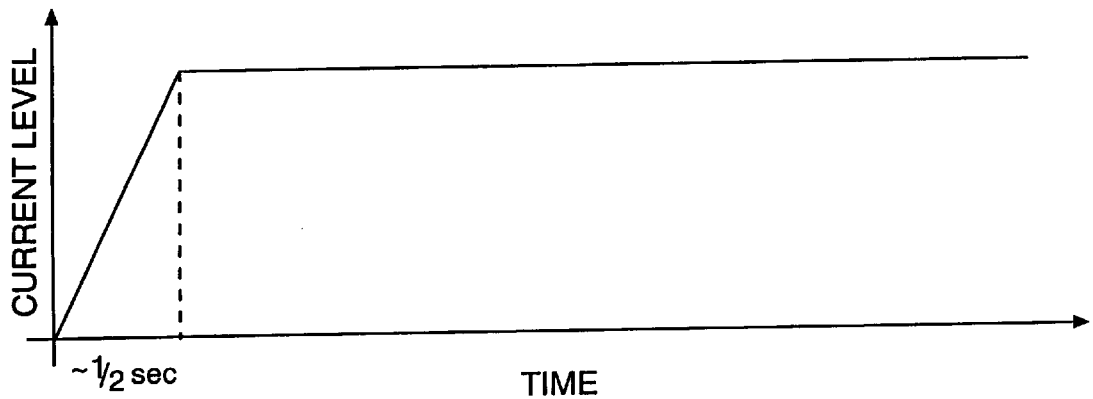
Figure 5:
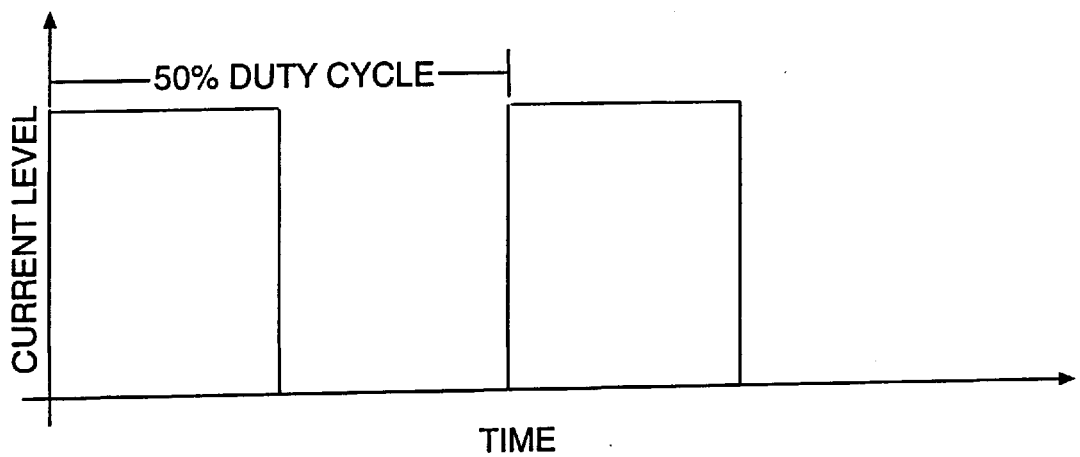

The waveform for the first treatment stage is shown in FIG. 5(*a*). The waveform for the first treatment stage is a modified square wave. For the first portion of each period, the waveform is a square wave characterized by a rapid rise to a high current level followed by a hold at that high current level. The second portion of each period is a gradual decay from the high current level to a level near zero. The waveform then repeats for the next period. In a preferred embodiment, the first portion of the waveform occurs for approximately ⅓ of the period and the second portion of the waveform occurs during the remaining ⅔ of the period.

The second treatment stage is intended to change the resistance of the injured tissue. It has been postulated that injured tissue has a higher electrical resistance than healthy tissue such that the flow of electrical impulses through an injured section of the body is different from normal. It has been further postulated that reducing the resistance back to normal would aid the healing process or otherwise reduce pain. To facilitate such change in tissue resistance, the electrodes receive a continuous direct current of between 300 $\mu$A and 1000 $\mu$A during the second treatment stage. Preferably, the current is between 400 $\mu$A and 650 $\mu$A. In addition, the polarity of the electrodes is preferably reversed at periodic intervals during this "charging" stage to avoid acid/base build-up in the injured tissue. While the charging stage may last for longer or shorter periods, the preferred method is for this stage to last 10 to 15 minutes.

The waveform for the second treatment stage is shown in FIG. 5(*b*). The waveform for the second treatment stage includes a non-repeating ramp period followed by a level period. The ramp period is preferably ½ second; the level period is preferably the remainder of the second treatment stage.

The third treatment stage is intended to promote healing in the injured tissue. During this healing stage, the electrodes receive pulsed direct current impulses of between 50 $\mu$A and 250 $\mu$A having a frequency of between 1 and 10 Hz and a duty cycle of between 30 and 70 percent. Preferably, the impulses are of 60 $\mu$A to 120 $\mu$A, at a frequency of 3 Hz, and a 50 percent duty cycle. While the healing stage may last for longer or shorter periods, the preferred method is for this stage to last 15 to 20 minutes.

The waveform for the third treatment stage is shown in FIG. 5(*c*). The waveform for the third treatment stage is a square wave of a particular duty cycle. For the first portion of each period, the waveform is a square wave characterized by a rapid rise to a high current level, a hold at that high current level, followed by a rapid return to near zero current. The second portion of each period is a hold at near zero current level. The waveform then repeats for the next period. The ratio of time at the high current level to the time period from one rapid rise to the next rapid rise is called the duty cycle. Preferably, the duty cycle is 50 percent, meaning that the two portions are of equal duration.

In a preferred embodiment, the three treatment stages are automatically executed sequentially, without any other intervening treatment stages. Such an arrangement overcomes problems of user forgetfulness and allows for the invention to be used on non-human subjects.

The description above has assumed that the tissue has been recently injured, such as a pulled muscle, or subjected to invasive medical treatment, such as reconstructive surgery on a knee. However, the method is also useful in treating chronic conditions such as pain from arthritic joints.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What we claim is:

1. A method for administering microcurrent electrotherapy treatment to a body comprising:

a) engaging an area of the body to be treated with a plurality of electrodes; and b) treating said area of the body by directing in sequence a series of different microcurrent treatments including:

i) in a first treatment stage, directing to the electrodes and into the area of treatment a pulsed direct current of between 10 $\mu$A and 100 $\mu$A having a frequency of between 100 and 500 Hz;

ii) in a second treatment stage, directing to the electrodes and into the area of treatment a continuous direct current of between 300 $\mu$A and 1000 $\mu$A; and iii) in a third treatment stage, directing to the electrodes and into the area of treatment a pulsed direct current of between 50 µA and 250 µA having a frequency of between 1 and 10 Hz and a duty cycle of between 30 and 70 percent.

2. The method of claim 1 wherein:
   a) said first treatment stage occurs for a time period of approximately 1 to 15 minutes;
   b) said second treatment stage occurs for a time period of approximately 7 to 20 minutes; and
   c) said third treatment stage occurs for a time period of approximately 3 to 20 minutes.

3. The method of claim 1 wherein the body to be treated is human.

4. The method of claim 1 wherein the body to be treated is a non-human animal.

5. The method of claim 1 wherein said third treatment stage immediately follows said second treatment stage.

6. The method of claim 5 wherein said second treatment stage immediately follows said first treatment stage.

7. An electrotherapy device for treating a variety of physical conditions comprising:
   a) a first power supply forming a part of the electrotherapy device and a first waveform generator for generating an electrical waveform and a first microprocessor controller for controlling the waveform generator;
   b) a pair of primary electrodes connected to said first waveform generator;
   c) wherein said first microprocessor controller being pre-programmed to cause said electrotherapy device to provide in sequence a series of three different microcurrent waveforms to an area of the body to be treated via said primary electrodes including:
      i) in a first treatment stage, a pulsed direct current waveform of between 10 µA and 100 µA having a frequency of between 100 and 500 Hz;
      ii) in a second treatment stage, a continuous direct current waveform of between 300 µA and 1000 µA; and
      iii) in a third treatment stage, a pulsed direct current waveform of between 50 µA and 250 µA having a frequency of between 1 and 10 Hz and a duty cycle of between 30 and 70 percent.

8. The device of claim 7 wherein said microprocessor controller is pre-programmed with a plurality of programs for generating different waveforms and further comprising a program selector for user selection between said programs.

9. The device of claim 7 further comprising:
   a) a second waveform generator associated with the electrotherapy device for generating an electrical waveform, and a second microprocessor controller for controlling the second waveform generator;
   b) a pair of secondary electrodes connected to said second waveform generator;
   c) wherein said second microprocessor controller is pre-programmed to cause said electrotherapy device to provide in sequence a series of three different microcurrent waveforms to an area of the body to be treated via said secondary electrodes including:
      i) in a first treatment stage, a pulsed direct current waveform of between 10 µA and 100 µA having a frequency of between 100 and 500 Hz;
      ii) in a second treatment stage, a continuous direct current waveform of between 300 µA and 1000 µA;
      iii) in a third treatment stage, a pulsed direct current waveform of between 50 µA and 250 µA having a frequency of between 1 and 10 Hz and a duty cycle of between 30 and 70 percent.

10. The method of claim 7 wherein each of the microcurrent treatments emits a current of 1000 µA or less.

11. The method of claim 10 wherein the continuous direct microcurrent treatment follows the pulsed direct microcurrent treatment.

12. A pre-programmed microcurrent electrotherapy device for sequentially treating a body area with a series of different programmed microcurrent treatments comprising:
   a) a power supply;
   b) a microcurrent waveform generator driven by the power supply and operative to generate three different preprogrammed microcurrent waveform including both pulsed direct and continuous direct waveforms;
   c) a microcurrent output operatively connected to the microcurrent waveform generator for transmitting microcurrent waveforms generated by the waveform generator to a treatment area; and
   d) a pre-programmed microprocessor coupled to the waveform generator for controlling the output of the microcurrent waveform generator, the microprocessor being programmed to cause the waveform generator to produce a sequence of different and separate programmed pulsed direct and continuous direct microcurrent waveforms that are transmitted to the body area being treated via the microcurrent output.

13. The preprogrammed microcurrent electrotherapy device of claim 12 wherein the programmed pulsed direct and continuous direct microcurrent waveforms produce microcurrent on the order of 1000 µA or less.

14. The preprogrammed microcurrent electrotherapy device of claim 13 wherein the sequence of programmed microcurrent waveforms generated by the waveform generator includes at least one continuous direct microcurrent waveform followed by a pulsed direct microcurrent waveform.

15. The preprogrammed microcurrent electrotherapy device of claim 13 wherein the sequence of programmed microcurrent waveforms generated by the waveform generator includes at least two separate pulsed direct microcurrent waveforms and wherein one of the pulsed direct microcurrent waveforms precedes the programmed continuous direct microcurrent waveform while the other pulsed direct microcurrent waveform follows the continuous direct microcurrent waveform.

16. The preprogrammed microcurrent electrotherapy device of claim 15 wherein the two programmed pulsed direct microcurrent waveforms include a microcurrent of approximately 10 to 250 µA while the programmed continuous direct microcurrent waveform includes a microcurrent of approximately 300 to 1000 µA.

17. A method for administering microcurrent electrotherapy to a body area comprising the steps of sequentially administering to the body area a series of different and pre-programmed microcurrent treatments wherein the pre-programmed microcurrent treatments sequentially administrated includes one treatment stage of a pulsed direct current waveform administered for a pre-selected time period, and a second treatment stage, independent of the one treatment stage, comprising a continuous direct current waveform administered for a second pre-selected period that remains generally constant over the second-preselected period.

18. The method of claim 17 wherein the pulsed direct current waveform comprises a series of pulses with each pulse including a trailing portion that ramps down from a relatively high current value to a relatively low current value.

19. The method of claim 18 wherein the pulsed direct current waveform comprises a series of direct current pulses separated by a third pre-selected time interval.

20. The method of claim 19 comprising sequentially directing to the body area a series of three separate and distinct microcurrent treatments including pulsed direct current treatments and continuous direct current of treatments.

21. The method of claim 20 wherein the pulsed direct microcurrent treatment includes a microcurrent of approximately 10 to 250 micro A directed to the body area while the continuous direct microcurrent treatment directs approximately 300 to 1000 micro A to the body area that is.

22. The method of claim 21 wherein each of the microcurrent treatments includes a distinctive current waveform and wherein the waveform of the pulsed direct current waveform reflects a duty cycle of approximately thirty to seventy percent.

23. The method of claim 22 wherein each of the microcurrent treatments includes a treatment period of approximately one to twenty minutes.

\* \* \* \* \*